United States Patent
Muller et al.

(10) Patent No.: US 11,579,017 B2
(45) Date of Patent: Feb. 14, 2023

(54) DIODE-PUMPED MULTIPASS CAVITY RAMAN GAS SENSOR AND METHOD OF USE

(71) Applicant: University of South Florida, Tampa, FL (US)

(72) Inventors: Andreas Muller, Tampa, FL (US); Juan Sebastian Gomez Velez, Tampa, FL (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 17/712,679

(22) Filed: Apr. 4, 2022

(65) Prior Publication Data

US 2022/0228911 A1 Jul. 21, 2022

Related U.S. Application Data

(63) Continuation-in-part of application No. PCT/US2020/053997, filed on Oct. 2, 2020.
(Continued)

(51) Int. Cl.
*G01J 3/44* (2006.01)
*G01J 3/02* (2006.01)
(Continued)

(52) U.S. Cl.
CPC ............. *G01J 3/4412* (2013.01); *G01J 3/021* (2013.01); *G01J 3/0208* (2013.01); *G01J 3/18* (2013.01);
(Continued)

(58) Field of Classification Search
CPC ........ G01J 3/4412; G01J 3/0208; G01J 3/021; G01J 3/14; G01J 3/28; G01J 3/18;
(Continued)

(56) References Cited

U.S. PATENT DOCUMENTS

| | | |
|---|---|---|
| 10,401,296 B1 | 9/2019 | Muller |
| 2002/0018496 A1* | 2/2002 | Gutin ..................... H01S 5/141 372/20 |

(Continued)

FOREIGN PATENT DOCUMENTS

WO 2013119320 A1 8/2013

OTHER PUBLICATIONS

International Search Report and Written Opinion dated Jan. 5, 2021 for parent PCT International Application No. PCT/US2020/053997.
(Continued)

*Primary Examiner* — Abdullahi Nur
(74) *Attorney, Agent, or Firm* — Molly L. Sauter; Smith & Hopen, P.A.

(57) ABSTRACT

A method for enhancement of spontaneous Raman scattering (SRS) from gases comprising a multimode blue laser diode which receives feedback from a near concentric bidirectional multipass cavity in such a way as to generate a circulating power of order 100 W for a sample volume of 10 mm³. The feedback, provided via a volume Bragg grating, reduces the laser bandwidth to 4 cm⁻¹. Spectra of spontaneous Raman scattering from ambient atmospheric air, detected collinearly with the pump, were recorded with a limit of detection below 1 part-per-million.

20 Claims, 9 Drawing Sheets

Related U.S. Application Data (60) Provisional application No. 62/909,474, filed on Oct. 2, 2019.

(51) Int. Cl.
  *G01J 3/18* (2006.01)
  *G01N 33/00* (2006.01)
  *G01J 3/12* (2006.01)
  *H01S 5/323* (2006.01)

(52) U.S. Cl.
  CPC .. *G01N 33/0009* (2013.01); *G01J 2003/1204* (2013.01); *G01J 2003/1213* (2013.01); *H01S 5/32341* (2013.01)

(58) Field of Classification Search
  CPC ....... G01J 2003/1204; G01J 2003/1213; G01J 3/44; G01N 33/0009; G01N 21/031; G01N 2021/651; G01N 21/65; H01S 5/32341; A61B 5/082
  See application file for complete search history.

(56) References Cited

U.S. PATENT DOCUMENTS

| | | | |
|---|---|---|---|
| 2003/0053049 A1* | 3/2003 | Fink | G01N 21/65 356/301 |
| 2008/0030728 A1 | 2/2008 | Nguyen | |
| 2012/0105827 A1 | 5/2012 | Carter et al. | |
| 2014/0071446 A1 | 3/2014 | Djeu et al. | |

OTHER PUBLICATIONS

Dewang Yang et al. "Highly sensitive Raman system for dissolved gas analysis in water" Applied Optics. vol. 55, No. 27, Sep. 2016, pp. 7744-7748.

Di Yan et al. "Highly Sensitive Broadband Raman Sensing of Antibiotics in Step-Index Hollow-Core Photonic Crystal Fibers" ACS Photonics, ACS Publications vol. 4, Jan. 2017, pp. 138-145.

Barbara M. Trabold et al. "Broadband high-resolution multi-species CARS in gas-filled hollow-core photonic crystal fiber" Optics Letters. vol. 42, No. 17, Aug. 2017, pp. 3283-3286.

Sebastian Schluter et al. "Demonstration of a signal enhanced fast Raman sensor for multi-species gas analyses at a low pressure range for anesthesia monitoring" Journal of Raman Spectroscopy. Wiley Online Library, wileyonlinelibrary.com/journal/jrs, May 2015, vol. 46, pp. 708-715.

Robert Salter et al. "Cavity-enhanced Raman spectroscopy with optical feedback cw diode lasers for gas phase analysis and spectroscopy" RSC Publishing, The Analyst, vol. 137, No. 20, Oct. 2012, pp. 4621-4868.

Dmitry Petrov et al. "High-Sensitivity spontaneous Raman spectrometer for gaseous media" Journal of Applied Spectroscopy, vol. 82, No. 1, Mar. 2015, pp. 120-124.

Dmitry V. Petrov "Multipass optical system for a Raman gas spectrometer" Applied Optics, vol. 55, No. 33, Nov. 2016, pp. 9521-9525.

Dmitry V. Petrov et al. "Pressure dependence of the Raman signal intensity in high-pressure gases" Journal of Raman Spectroscopy, Wiley Online Library, wileyonlinelibrary.com/journal/jrs, Oct. 2016.

B. Petrak et al. "Isotopic gas analysis through Purcell cavity enhanced Raman scattering" Applied Physics Letters, vol. 108, Mar. 2016, Sep. 11, 2007.

Benjamin Petrak et al."Purcell Enhancement of Raman Scattering from Atmospheric Gases in a High-Finesse Microcavity" CLEO: 2013 Technical Digest.

Wolfram Miekisch et al. "Diagnostic potential of breath analysis—focus on volatile organic compounds" Clinica Chimica Acta, vol. 347, Apr. 2004, pp. 25-39.

P Malfertheiner et al. "Current concepts in the management of Helicobacter pylori infection: the Maastricht III Consensus Report" Helicobacter Pylori. Gut, 2007, vol. 56, pp. 772-781.

J Kiefer et al. "Design and characterization of a Raman-scattering-based sensor system for temporally resolved gas analysis and its application in a gas turbine power plant" Measurement Science and Technology, vol. 19, 2008, 9pp.

R.A Hill et al. "Retroeflecting multipass cell for Raman scattering" Applies Optics, vol. 16, No. 7 , Jul. 1977, pp. 2004-2006.

Tobias Jochum et al. "Multigas Leakage Correction in Static Environmental Chambers Using Sulfur Hexafluoride and Raman Spectroscopy" ACS Publications, Analytical Chemistry, Oct. 2015, vol. 87, pp. 11137-11142.

Timothy M. James "Trace gas and dynamic process monitoring by Raman spectroscopy in metal-coated hollow glass fibres" Analytical Methods, Feb. 7, 2015, pp. 2568-2576.

Stefan Hanf et al. "Fast and Highly Sensitive Fiber-Enhanced Raman Spectroscopic Monitoring of Molecular H2 and CH4 for Point-of-Care Diagnosis of Malabsorption Disorders in Exhaled Human Breath" ACS Publications, American Chemical Society, Dec. 2014, pp. 982-988.

Stefan Hanf et al. "Fiber-Enhanced Raman Multigas Spectroscopy: A Versatile Tool for Environmental Gas Sensing and Breath Analysis" ACS Publications, American Chemical Society. May 2014, pp. 5278-5285.

M. Gaft et al. "UV gated Raman spectroscopy for standoff detection of explosives" Optical Materials, vol. 30, Jan. 2008, pp. 1739-1746.

David A Armbruster et al. "Limit of Blank, Limit of Detection and Limit of Quantitation " Clin Biochem Rev vol. 29 Suppl Aug. 2008, pp. S49-S52.

R.L. Aggarwal et al. "Raman spectra and cross sections of ammonia, chlorine, hydrogen sulfide, phosgene, and sulfur dioxide toxic gases in the fingerprint region 400-1400 cm-1" AIP Advances 6, 025310, Feb. 2016, pp. 1-7.

International Preliminary Report on Patentability dated Apr. 14, 2022 for parent PCT International Application No. PCT/US2020/053997.

* cited by examiner

DIODE-PUMPED MULTIPASS CAVITY RAMAN GAS SENSOR AND METHOD OF USE

CROSS-REFERENCE TO RELATED APPLICATIONS

The present invention is a continuation-in-part of and claims priority to PCT/US2020/053997, filed on Oct. 2, 2020, which claims priority to U.S. Provisional Patent Application No. 62/909,474 filed on Oct. 2, 2019, the entirety of which are incorporated herein by reference.

FEDERALLY SPONSORED RESEARCH OR DEVELOPMENT

This invention was made with Government support under Grant No. NSF-ECCS 2116275 awarded by the National Science Foundation. The government has certain rights in the invention.

BACKGROUND OF THE INVENTION

Sensing and monitoring of the chemical composition of gases is needed for a variety of applications, including, but not limited to, medical diagnostics, process control, environmental surveying and hazard detection. Gas sensing systems capable of detecting trace concentrations are particularly desirable and should provide long-term reliability with rapid response times and economic feasibility. In addition, a gas sensing system able to differentiate isotopologes—molecules differing only by their isotopic composition—finds applications in precision spectroscopy and tracing applications.

Although a host of readily available techniques for trace gas detection currently exist, including ion mobility spectrometry, absorption spectroscopy, non-dispersive infrared spectroscopy and ion mass spectrometry, the overall size, complexity and price of these techniques have prevented the realization of a miniaturized, consumer viable product for trace gas detection. Additionally, with the rapid development of "smart" electronic devices that now reach into a realm of household applications, a compact, low-cost trace gas analyzer could find numerous applications in portable health diagnostics, home monitoring, etc.

As a conceptually simple, versatile, isotopically sensitive, and extremely reliable optical technique, spontaneous Raman scattering (SRS) is, in principle, poised to realize such applications. However, the low density of gases to be detected and the notoriously weak scattering cross-section of SRS have precluded its application in an economical fashion. Numerous practical difficulties have so far precluded gas phase SRS at parts-per-billion (ppb) concentrations.

Accordingly, what is needed in the art is an improved system and method based upon spontaneous Raman scattering (SRS) that is applicable for sub-parts-per-million (ppm) detection of gases, while also being compact and economical.

SUMMARY OF INVENTION

In various embodiments, the present invention provides a system employing multipass cavity Raman scattering for practical, compact and economical trace gas sensing. In an exemplary embodiment, the system of the present invention includes a high-power multimode laser diode emitting light that is coupled into a near-concentric two-way multipass cavity, thereby creating a closed path for the laser light, resulting in an external cavity diode laser with a cavity length on the order of meters. A volume Bragg grating is additionally incorporated as a spectrally selective element to reduce the laser linewidth to below 0.1 nm (4 cm$^{-1}$). Beam correction optics are additionally included in the system to create sub-mrad laser beam divergence and a dichroic filter collinearly extracts the forward and backward Raman scattered light. In an exemplary embodiment of the present invention, Raman spectra is recorded using the novel system, in unpressurized ambient air and in unpressurized breath, using different spectral analyzers, including one based on an uncooled low-cost CMOS camera. The system can accomplish detection with limits below 1 ppm at an exposure time of order one minute.

In one embodiment, the present invention provides a gas sensor system comprising, a bidirectional multipass cavity to receive a sample gas, a multimode laser diode to emit a laser light beam, the beam having a laser linewidth, an aspheric lens positioned to collimate the beam emitted from the laser diode along a fast diverging axis, a cylindrical mirror positioned to receive the beam from the aspheric lens, to remove divergence along a slow diverging axis of the beam and to remove astigmatism of the beam. The system further includes, a diffraction grating to receive the beam reflected from cylindrical mirror, to reduce the linewidth of the beam and to feedback the beam having the reduced linewidth to the multimode laser diode, a focusing lens to receive the beam from the diffraction grating and to focus the beam into the bidirectional multipass cavity and a spectral analyzer to collect spectra of spontaneous Raman scattering from the interaction of the beam with the sample gas.

In a specific embodiment, the bidirectional multipass cavity comprises a first concave spherical mirror and a second concave spherical mirror positioned in near concentric arrangement and the beam is reflected between the first mirror and the second mirror approximately 80 times through the gas sample and cross at two slightly longitudinally offset foci to generate a high intensity beam that is returned to the focusing lens. The first concave spherical mirror and the second concave spherical mirror of the multipass cavity may have a radius of curvature of about 50 mm and be separated from each other by about 97 mm.

In a particular embodiment, the spectral analyzer is positioned collinearly with the multimode diode laser and the spectral analyzer comprises a dichroic filter to collinearly extract forward and backward Raman scattered light.

In an additional embodiment, the present invention provides a method for trace gas sensing, the method which includes, introducing a sample gas into a bidirectional multipass cavity, coupling a laser light beam emitted from a multimode laser diode to the multipass cavity, the beam having a laser linewidth, collimating the beam emitted from the laser diode along a fast diverging axis using an aspheric lens and removing divergence along a slow diverging axis of the beam and removing astigmatism of the beam using a cylindrical mirror positioned to receive the beam from the aspheric lens. The method further includes, reducing the linewidth of the beam and feeding back the beam having the reduced linewidth to the laser diode using a diffraction grating to receive the beam reflected from cylindrical mirror, focusing the beam from the diffraction grating using a focusing lens to couple the beam into the bidirectional multipass cavity and collecting spectra of spontaneous Raman scattering from the interaction of the beam with the sample gas in the multipass cavity using a spectral analyzer.

Accordingly, the present invention provides an improved system and method based upon spontaneous Raman scattering (SRS) that is applicable for sub-ppm detection of gases, while also being compact and economical. Various benefits of the present invention include the ability to detect trace constituents and isotopologues in complex gas mixtures such as breath.

BRIEF DESCRIPTION OF THE DRAWINGS

For a fuller understanding of the invention, reference should be made to the following detailed description, taken in connection with the accompanying drawings, in which.

DETAILED DESCRIPTION OF THE INVENTION

Spontaneous Raman scattering (SRS) is ideally suited for trace gas detection due to its simplicity and versatility. However, the intensity of Raman scattered light from a gas sample is typically low, particularly when detecting at trace concentrations. Spontaneous Raman scattering thus, at a minimum, requires a powerful laser with high spectral purity, which can be complex, expensive and can consume a large amount of power.

A substantial advantage of spontaneous Raman scattering (SRS) is the possibility of simultaneously detecting a large number of chemical species using a single laser source and a single detector. However, one of the most common impediments to providing a cost-effective implementation of SRS is the high cost of a stable multi-Watt laser source. Laser light for SRS is typically derived from a diode-pumped solid-state laser, and in particular, a frequency-doubled 1064 nm laser is commonly used. To overcome the expense and complexity associated with a multi-Watt level narrow bandwidth laser of this kind, the embodiments of the present invention instead utilize a single high-power semiconductor laser diode at 443 nm as the pump light source. In a particular embodiment, the semiconductor laser diode implemented in the present invention may be a GaN laser diode rated up to 6 W. In addition to the advantage of the increased Raman scattering cross-section due to the shortened wavelength of the semiconductor laser diode, there is considerable benefit in cost, size, and power efficiency associated with the use of the semiconductor laser diode. However, the employment of a multimode laser diode introduces several obstacles, including an enlarged spectral bandwidth and a need for beam correction.

Figure 1:
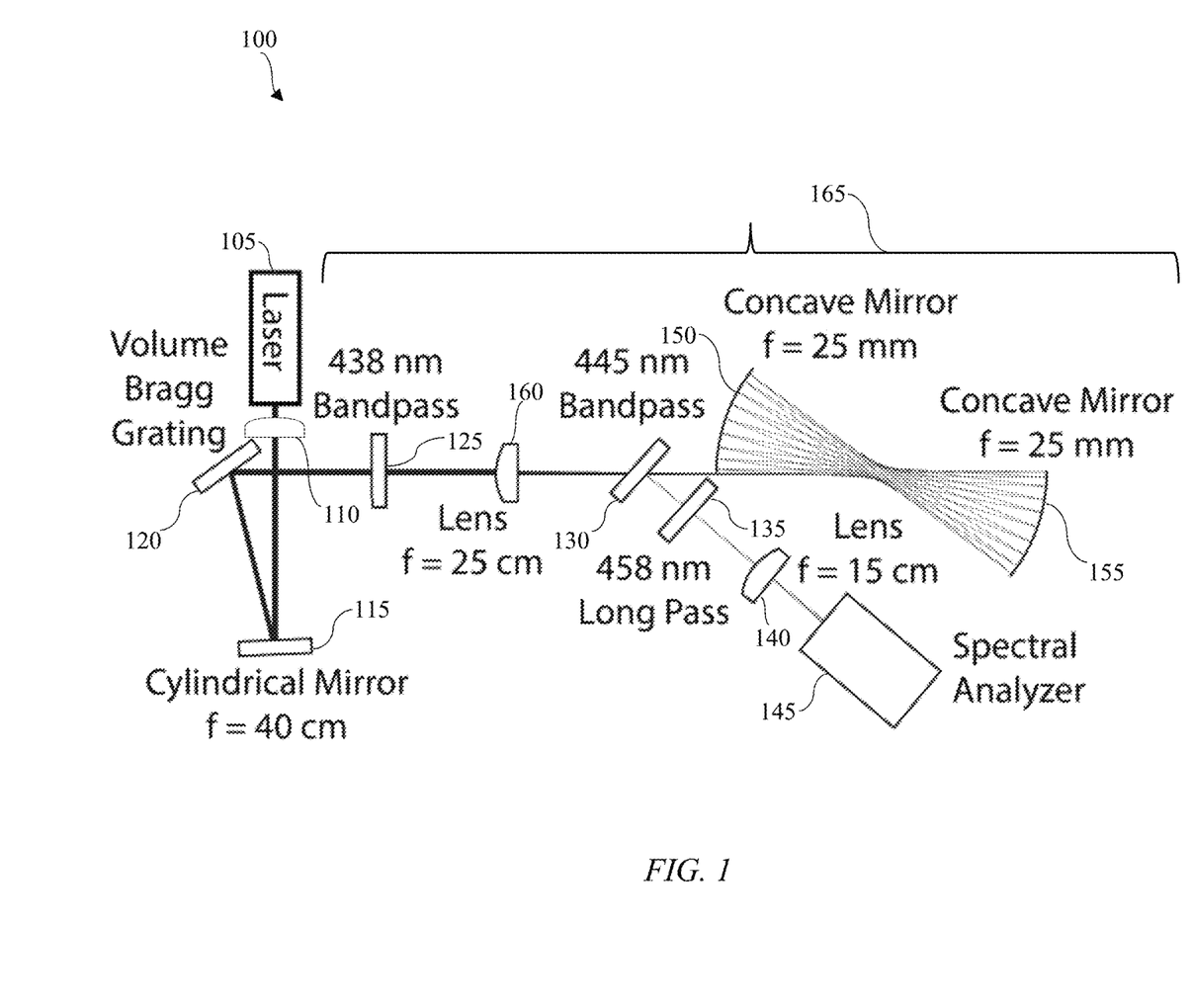
FIG. 1 illustrates a gas detection system in accordance with an embodiment of the present invention.

FIG. 1 illustrates an exemplary embodiment of the gas detection system 100 in accordance with the present invention. In general, the present invention creates an external cavity diode laser for which the external cavity is long (several meters) and in which the beam overlaps itself near two foci. This configuration enables high laser power circulating in a relatively small volume but requires overcoming the obstacles which largely originate from the multimode properties of the laser diode.

In a particular embodiment, the gas detection system 100 of the present invention includes a semiconductor laser diode 105 emitting a laser beam having a fast diverging axis and a slow diverging axis. In a particular embodiment, the semiconductor laser diode may be a GaN diode operating at 443 nm. A cylindrical mirror 115 is positioned to remove divergence along the slow diverging axis of the beam and to reduce astigmatism. In a particular embodiment, the cylindrical mirror 155 may have a focal length of 40 cm. A diffraction grating 120 is positioned to receive the beam reflected from the cylindrical mirror 115, to provide a beam having high spectral selectivity to the multipass cavity 165 and to provide the beam returning from the multipass cavity 165 to the laser diode 105, thereby providing feedback to the laser diode. The multipass cavity 165 comprises two concave mirrors 150, 155.

One obstacle to the use of semiconductor diode lasers in SRS is the need for beam correction. The beam emerging out of the bare multimode laser diode is astigmatic and diverges differently along the fast diverging and slow diverging axis. Another obstacle to the use of a semiconductor diode laser in SRS is the requirement for laser stabilization via feedback. The spectral bandwidth the light generated by the bare multimode laser diode is on the order of several nanometers, which exceeds the typical linewidth of rotationally resolved, or rotationally collapsed, Raman spectra in atmospheric air (~0.1 cm$^{-1}$) by about three orders of magnitude. Therefore, for high-resolution applications, for example in isotopologue spectroscopy, it is desirable to reduce the laser linewidth.

In the present invention, to overcome the obstacles introduced by the use of a semiconductor diode 105, the aspheric lens 110 is used to collimate the beam emitted from the diode 105 along the fast diverging axis. In a specific embodiment, the aspheric lens 110 may have a numerical aperture of 0.5 and an effective focal length of 4 mm. The cylindrical mirror 115 is additionally positioned to remove the remaining divergence along the slow diverging axis of the beam and to reduce astigmatism. In a specific embodiment, the cylindrical mirror 115 may have a focal length of 40 cm. The resulting beam properties may have dimensions of approximately 5 mm with divergences of less than about 0.5 mrad along the slow axis and dimensions of approximately 4 mm with divergences of less than about 0.1 mrad along the fast axis.

Additionally, the volume Bragg grating 120 (Optigrate, >90% diffraction efficiency, <0.1 nm bandwidth) is employed to provide high spectral selectivity for light that reaches the mirrors 150, 155 of the multipass cavity 165 and returns to retrace its path, thereby providing feedback to the laser diode 105. In an alternative embodiment, the volume Bragg grating 120 can be replaced with an ordinary diffraction grating. When receiving feedback by the multipass cavity 165, coupled through the grating 120, the laser linewidth is reduced to below 0.1 nm (4 cm$^{-1}$). Throughout the illustrated setup in FIG. 1, it is understood that the beam is propagating in a horizontal plane with a linear in-plane polarization.

The multipass cavity 165 includes the near concentric arrangement of two concave spherical mirrors 150, 155 (radius of curvature of 50 mm) with a mirror separation of about 97 mm. With this configuration of the mirrors 150, 155, a beam grazing the first mirror gets reflected about 40 times before retracing itself providing approximately 80 total reflections through the sample volume. The light beam crosses at two foci, slightly offset longitudinally, at which a high intensity is generated. The number of achievable reflections is limited by the ratio of the solid angle of each curved mirror 150, 155 and that of the beam. For this reason, a focusing lens 160 with relatively long focal length of about f=25 cm is used to introduce the beam into the cavity. The total optical path length in the cavity is estimated to be approximately 7.5 m, thereby providing the long external cavity.

In conventional gas phase SRS, a side detection geometry is most often employed for the collection of the Raman scattered light, because of its ability to effectively avoid background light introduced with, or created by, the strongly focused laser pump beam. However, a perpendicular excitation/detection geometry for side detection requires that the pump light beam be tightly focused, placing further constraints on the pump laser mode quality and the detection resolution.

In the present invention, in order to employ a multimode laser diode as the pump, a collinear geometry is utilized here instead of a side detection geometry. Although this collinear geometry requires careful elimination of background signals, it also provides significant benefits by relaxing beam overlap requirements in the multipass cell and allowing for an eventual back-reflection with collection of both forward and backward Raman scattered light. In addition, with this arrangement, the total intensity, $I_{SRS,tot}$, of the Raman scattered light ultimately collected is the sum of the intensities into each direction of the multipass arrangement, so that $I_{SRS,tot} \propto N\, I_{laser}$, where N is the number of reflections (neglecting mirror losses). Since, $I_{laser}$, the laser intensity at each of the foci, itself scales with N, it follows that $I_{SRS,tot}$ scales with the square of N. In the present invention, the backward Raman scattered light is first filtered using a tilted bandpass filter 130 and a long pass filter 135 and then coupled into a multimode optical fiber 145 (62.5 μm core diameter) using an off-axis parabolic reflector 140 (Thorlabs RC04FC-P01) for spectral analysis.

Due to the collinear detection geometry, particular attention was devoted to the reduction of various background signals that co-propagate with the detection beam. Prior to entering the multipass cavity 165, the laser light was first filtered with a bandpass filter 125 (Semrock FF01-438/24-25) to remove any fluorescence from the laser diode or from optical components traversed by the beam upstream. The tilted bandpass filter 130 (Semrock FF01-445/20-25), reflecting the Raman scattered light returning from the multipass cavity 165, also serves as a secondary prefilter for the incoming beam. Finally, the long pass filter 135 (Semrock LP02-458RS-25) was positioned in the Raman collection path to remove background light at the laser frequency and background light generated by the residual laser reflections inside of optical components, in particular inside the collection lens. The remaining background light originated where the incoming laser beam grazes the curved mirror. A compromise must be found between the number of reflections (limited by the proximity of the incoming beam to the edge), and the amount of background light. The remaining background light (polarized identically to the signal) is as seen in the data shown, i.e., no subtraction and/or correction was performed.

In general, FIG. 1 illustrates a gas detection system 100 in accordance with an embodiment of the present invention, wherein a collimated pump light from a semiconductor laser diode 105 is focused near the center of a near concentric multipass cavity 165 comprises two mirrors 150, 155. Spontaneous Raman emission is collected collinearly and the volume Bragg grating 120 makes the feedback from the multipass cavity 165 spectrally selective, reducing the laser linewidth to less than 4 cm$^{-1}$.

In various embodiments, the present invention provides a system that integrates a low-cost, high-power, multimode laser diode 105 into a multipass cavity 165, effectively creating an external cavity diode laser having a cavity length of several meters out of which a high flux of Raman scattered photons can be generated. As such, high circulating laser power (<100 W) and narrow linewidth (<0.1 nm) can be obtained at a low cost with a small sourced input power (2 W). Gases, such as ambient methane (approximately 2 ppm concentration), can be detected using the system of the present invention, under atmospheric conditions, with a limit of detection well below 1 part-per-million (ppm).

Various embodiments of the present invention may be used for chemical gas sensing at trace concentrations in numerous applications, including, but not limited to, medical diagnostics, hazardous gas monitoring, environmental detection and isotopic detection. In particular, the gas detection system of the present invention is applicable to the urea breath test, which requires isotopologue differentiation.

Figure 2:
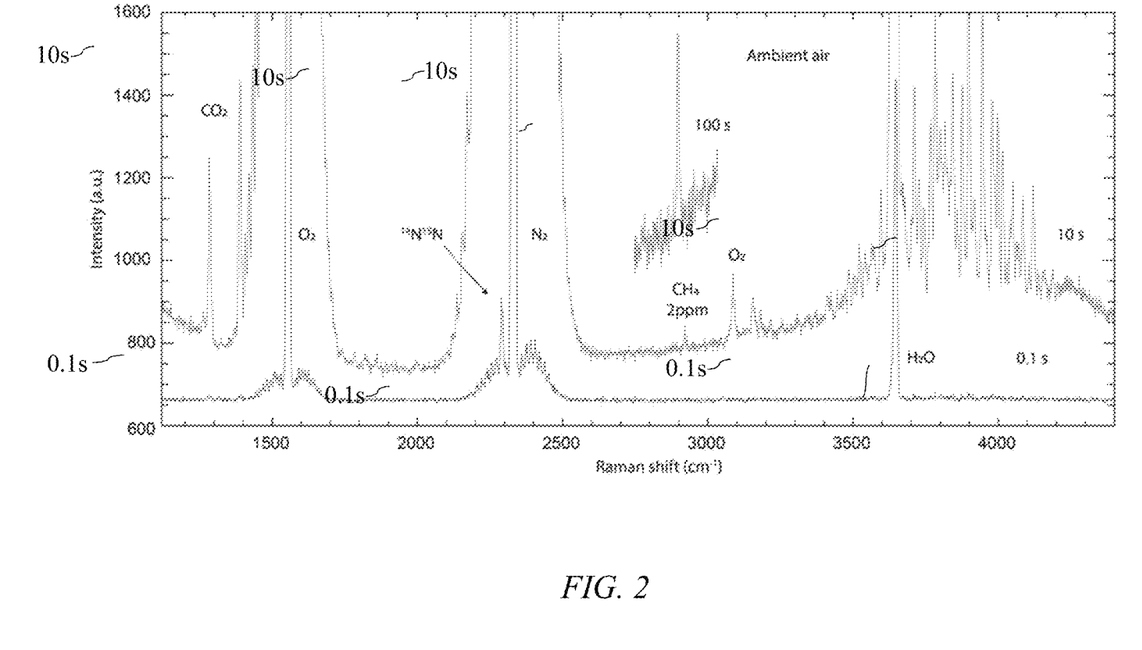
FIG. 2 illustrates a spectral overview of the simultaneous detection of five chemical species found in ambient laboratory air at varying concentrations with detection resolution of 10 cm$^{-1}$ and exposure times of 0.1 seconds, 10 seconds, and 100 seconds are illustrated, in accordance with an embodiment of the present invention.

Measurements have been performed on both ambient air and breath to illustrate the ability to distinguish different trace constituents of known concentration. FIG. 2 illustrates a spectral overview of the simultaneous detection of five chemical species found in ambient laboratory air at varying concentrations with detection resolution of 10 cm$^{-1}$ and exposure times of 0.1 seconds, 10 seconds, and 100 seconds are illustrated, in accordance with an embodiment of the present invention. FIG. 2 provides an overview of a measurement of ambient laboratory air (relative humidity of about 40%) spanning Raman shifts from 1100 cm$^{-1}$ to 4400 cm$^{-1}$ for exposure times of 0.1 s and 100 s. As can be seen, spectral signatures of numerous molecular species are detectable within seconds, including nitrogen (78%), oxygen (21%), water (0.7%), carbon dioxide (400 ppm), and methane (2 ppm). Isotopic nitrogen gas $^{14}N^{15}N$ is also measurable. The possibility of clearly resolving the ambient methane SRS peak at 2914 cm$^{-1}$ suggests sub-ppm limits of detection for methane, given that its ambient concentration is less than 2 ppm. It is also noted that in all the measurements presented the solid angle for collection of the Raman scattered light was less than 0.1 sr (steradian), implying that only a very small fraction of the total Raman emission generated is actually being collected, indicating significant room for improvements.

Figure 3:
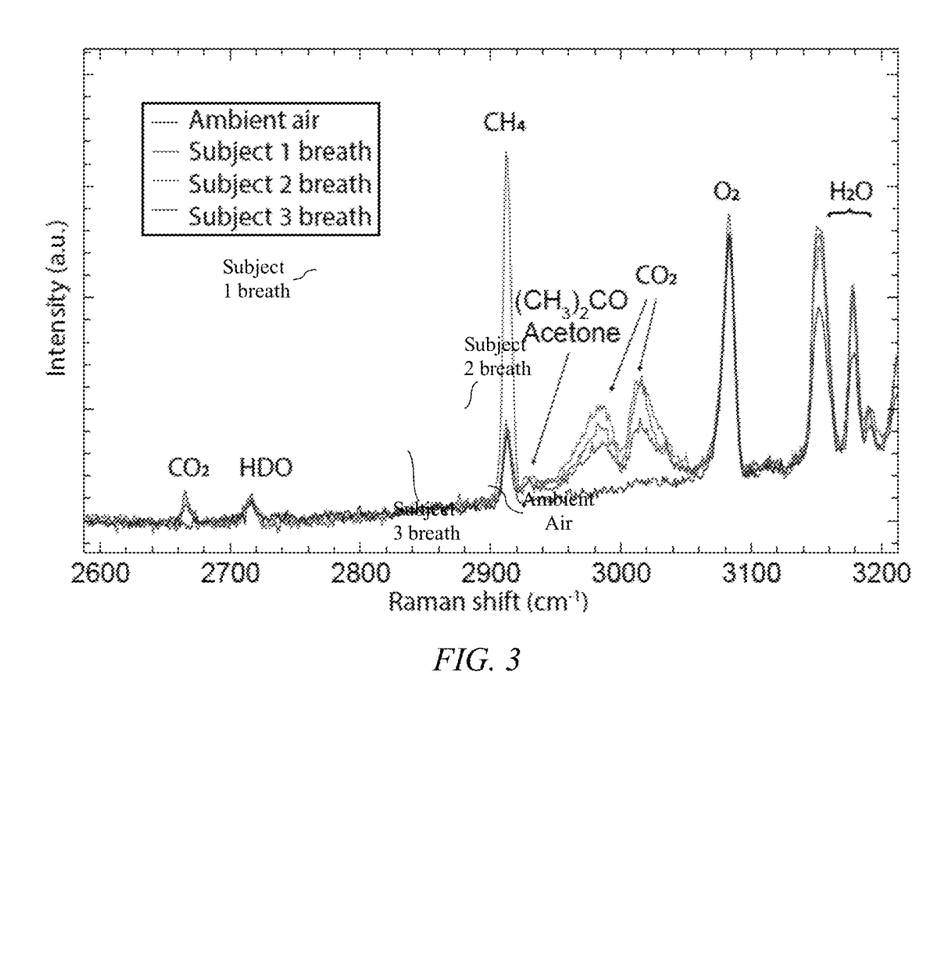
FIG. 3 is a graphical illustration of the comparison of laboratory ambient air and breath samples from three subjects displaying trace concentrations of hydrocarbons in breath with 100 s exposure times.

FIG. 3 is a graphical illustration of the comparison of laboratory ambient air and breath samples from three subjects displaying trace concentrations of hydrocarbons in breath with 100 s exposure times. FIG. 3 shows measurements of a set of three breath samples, detected in the range between 2600-3200 cm$^{-1}$, at an exposure time of 100 s. To make these measurements, exhaled air was blown into the center of the multipass cavity 165 using a teflon tube with a 4.5 mm diameter. No effort was made at retaining the introduced air, which intermixed with laboratory air in the detection region. Nonetheless, in addition to nitrogen, oxygen, water and carbon dioxide signatures, a peak at 2918 cm$^{-1}$ due to acetone is also seen. Acetone is known to be present in human breath at levels on the order of 1 ppm. In addition, the presence of methane can also be measured in breath. The practicality of the setup is evident from the data of FIG. 3 because many other trace constituents, such as carbon monoxide, ammonia, nitric oxide, and many hydrocarbons are present in breath at concentrations comparable to that of acetone. Furthermore, hazardous gases, such as chlorine, hydrogen sulfide, phosgene, and sulfur dioxide could easily be monitored at sub-ppm levels due to comparable Raman scattering cross sections. As such, the apparatus of the present invention is capable of providing concentrations of more than a dozen molecular species in a simultaneous measurement on the order of minutes.

Figure 4:
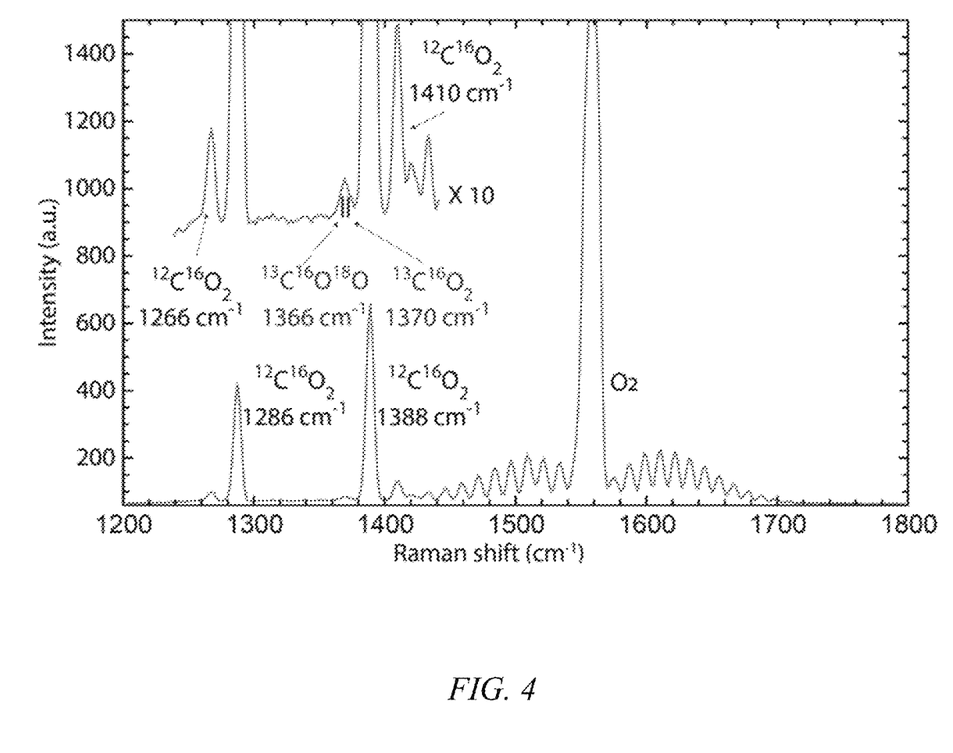
FIG. 4 is a graphical illustration of isotopically sensitive measurements of carbon dioxide in breath (ambient environment) with spectral detection resolution of 7 cm$^{-1}$, in accordance with an embodiment of the present invention.

Lastly, it is shown how the apparatus of the present invention can perform isotopologue analysis. FIG. 4 is a graphical illustration of isotopically sensitive measurements of carbon dioxide in breath (ambient environment) with spectral detection resolution of 7 cm$^{-1}$, in accordance with an embodiment of the present invention. FIG. 4 illustrates a measurement of breath for Raman shifts between 1200 cm$^{-1}$ and 1800 cm$^{-1}$. Spectral signatures from carbon dioxide and oxygen dominate in this range, with carbon 12 and oxygen 18 as the primary atomic constituents. Additionally, a peak originating in Raman scattering from carbon 13 is also visible (arrow in FIG. 4). This peak is actually nearly overlapping with a peak due to Raman scattering from $^{12}C^{18}O^{16}O$, as indicated. Considering the natural abundances of $^{13}CO_2$ (1.1%) and $^{12}C^{18}O^{16}O$ (0.4%), the peak near 1368 cm$^{-1}$ is expected to have a magnitude near 1.5% that of the peak at 1388 cm$^{-1}$, which is close to the ratio extracted from the data of FIG. 4. The possibility of easily detecting carbon isotopologues has applications for example as a $^{13}C$ urea test, with which metabolic pathways of ingested isotopologue rich substances can be diagnosed.

The measurements of FIGS. 2-4 reveal selectivity and sensitivity of Raman scattering in gases significantly improved over previously reported approaches. In particular, considering the still rather modest input laser power of about 1.9 W and the lack of any pressurization or gas containment in the sample region, a detection limit substantially lower than previously demonstrated is possible with the simple multipass cavity/external cavity technique, in accordance with the present invention. In the current embodiment, limits of detection can already reach below 1 parts-per-million for methane and for most molecular species with comparable Raman scattering cross-section. Table I summarizes figures for the limit of detection (LOD) for selected molecules following previously known procedures described in the literature.

TABLE 1

Limit of detection (LOD) for trace concentrations of exhaled gases for two exposure times, with cross sections normalized to those of nitrogen (2331 cm$^{-1}$).

| gas | shift | cross sec. | 5 s LOD | 100 s LOD |
| --- | --- | --- | --- | --- |
| $CO_2$ | 1388 cm$^{-1}$ | 1.1 | 34 ppm | 8.6 ppm |
| $(CH_3)_2CO$ | 2934 cm$^{-1}$ | 10.0 | | 0.5 ppm |
| $CH_4$ | 2917 cm$^{-1}$ | 8.6 | 740 ppb | 470 ppb | a.

The respective scattering cross sections are also listed as ratios to the $N_2$ cross section. The enhancement provided by the bidirectional multipass cavity 165 is such that practically any molecular analyte can be detected in the low ppm range with exposure times of seconds. An advantage of short exposures is that cooled array detectors for spectral analysis are not needed. Thermoelectrically cooled detectors, although widely available, are an impediment to miniaturization of SRS trace detection systems due to increased size and power consumption. When ambient detectors can be employed, the cost and complexity of spectral analysis is dramatically reduced.

As a point of illustration, the data of FIG. 4 was recorded with a spectral analyzer that consisted of a 3600 grooves/mm holographic diffraction grating (Thorlabs) and a room temperature CMOS array detector (QHYCCD minicam) equipped with a 16 mm focal length camera lens. The incoming light was delivered over a 62.5 µm multimode optical fiber collimated with an off-axis parabolic reflector (Thorlabs RC08FC-P01). The overall resulting detection system could be made portable and compact with a form factor comparable to that of a textbook.

In addition, curved mirrors with a larger solid angle can significantly increase the number of passes and thus the scattered Raman light intensity. Finally, noting that in the current setup the SRS collection occurs in a solid angle of less than 0.1 sr, significant gains may be made by improving the collection efficiency, possibly by way of the Purcell effect.

In an additional embodiment, the system and method of the present invention can be extended to operate under pressure so that samples can be compressed and introduced into the multipass cavity. The spontaneous Raman scattering rate of pressurized gas samples is greatly enhanced inside a near-concentrical optical cavity. With the addition of a pressurization box, a significant decrease in LOD can be obtained with the approach described herein. Assuming pressurization to 40 bar, detection limits for methane in the 10 ppb (parts per billion) range can be expected.

Figure 5:
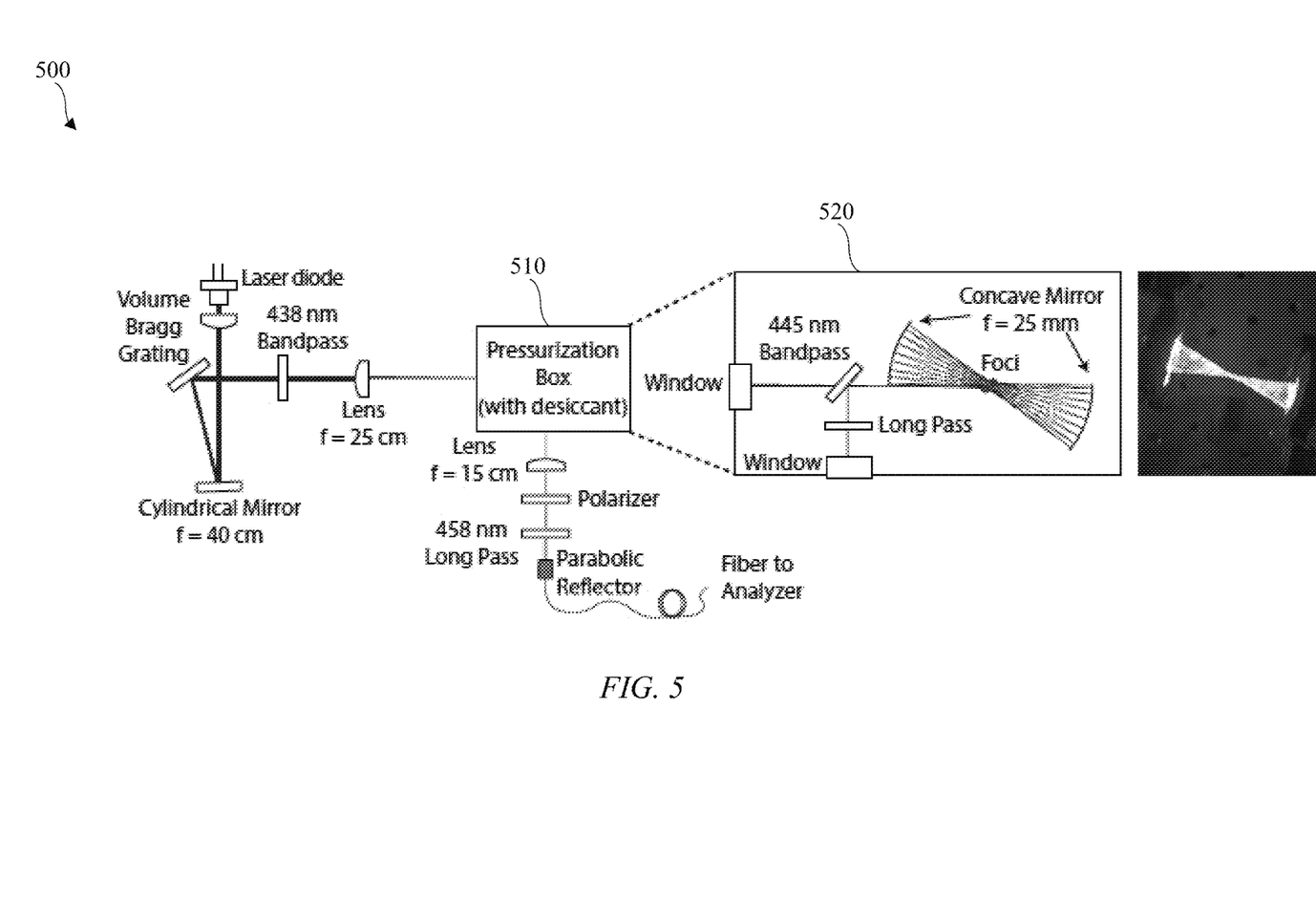
FIG. 5 illustrates a gas detection system comprising a pressurization box containing the multipass optical cavity, in accordance with an embodiment of the present invention.

A system 500 comprising a pressurization box 510 is illustrated with reference to FIG. 5. As illustrated, a beam from a semiconductor laser diode is focused to the center of a multipass optical cavity 520 inside of a pressurization box 510 in such a way that the beam returns, retracing its path. The bandpass filter of the multipass optical cavity 520 inside the pressurization box 510 allows for collinear collection while the feedback from the cavity 520 is spectrally selective (volume Bragg grating) to reduce the laser linewidth to less than 4 cm$^{-1}$. The effective circulating power exceeds 80 W, as estimated by the number of passes and taking into account laser feedback (at 1.8 A laser diode current).

In this embodiment, pressurization of the box 510 up to 10 atm was performed with a hand pump for the purpose of increasing the molecular number density. Prior to pressurization of the chamber was evacuated with a mechanical roughing pump and desiccant (silica gel beads) was placed inside the chamber to remove moisture. In order to minimize distortions of the cavity path as the pressure in the chamber is increased, the two mirrors making up the multipass cavity were held on a separate plate attached to the chamber via a pedestal. The chamber assembly was made rigid enough that measurements could be performed without realignment of the optics when changing gas samples.

In an experimental embodiment, systematic SRS measurements were performed with ambient air and human breath in the chamber. FIG. 2 shows a broad overview of SRS spectral intensity for such samples. All peaks seen in this window (1200 to 4500 cm$^{-1}$) are from rotation-vibration Raman bands from $N_2$, $O_2$, $CO_2$, $H_2O$, $CH_4$, $H_2$, and some of their isotopologues, as indicated. Ambient air was that of the laboratory (relative humidity of approximately 30%) and was directly pumped into the chamber. The breath sample was first collected into a plastic bag and then pumped into the chamber. Despite the significantly larger humidity of breath compared to ambient air, the desiccant removed water effectively for both, with a common residual water concentration of approximately 100 ppm. No background subtraction or field correction was performed. The total exposure time was 5 s for the spectral range from 1150 to 2600 cm$^{-1}$ and 5 min for the spectral range from 2850 to 4200 cm$^{-1}$. The average pressure in the chamber was 7.5 bar.

Figure 6:
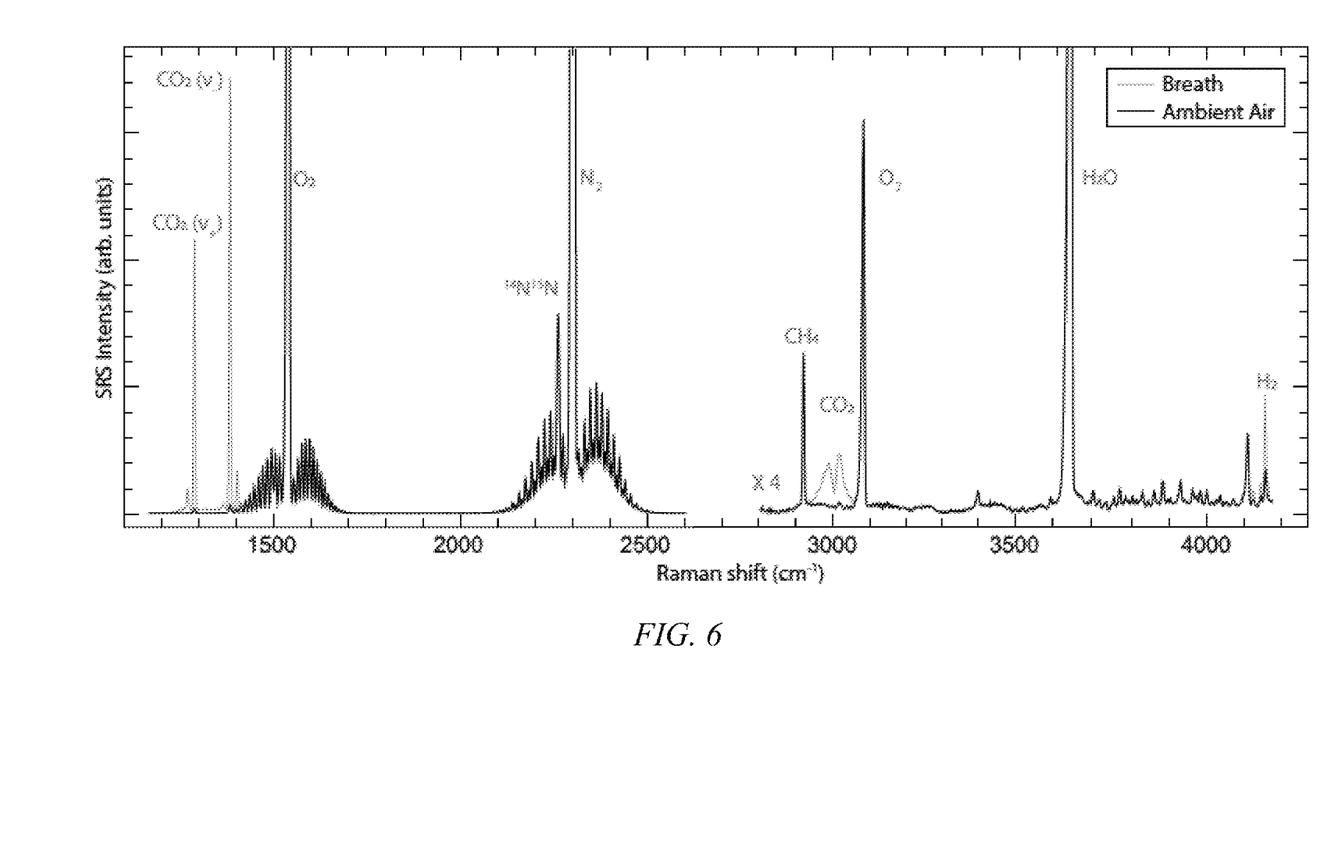
FIG. 6 illustrates a spectral overview of simultaneously detected chemical species found in breath and ambient air with exposure times of 5 s and 5 min for Raman shifts 1150 to 2600 cm$^{-1}$ and 2850 to 4200 cm$^{-1}$, respectively, wherein measurements are taken at 7.5 bar pressure, in accordance with an embodiment of the present invention.

Although the spectrum of FIG. 6 is dominated by peaks originating from the molecular species of the highest concentration, e.g., nitrogen and oxygen, peaks due to trace constituents are readily identified without any data processing. Most obviously the presence of methane at ≈1.9 ppm ambient concentration is certified by the presence of the peak at 2917 cm$^{-1}$, but also the presence of hydrogen with an ambient concentration of less than 600 ppb is clear (4160 cm$^{-1}$).

Figure 7:
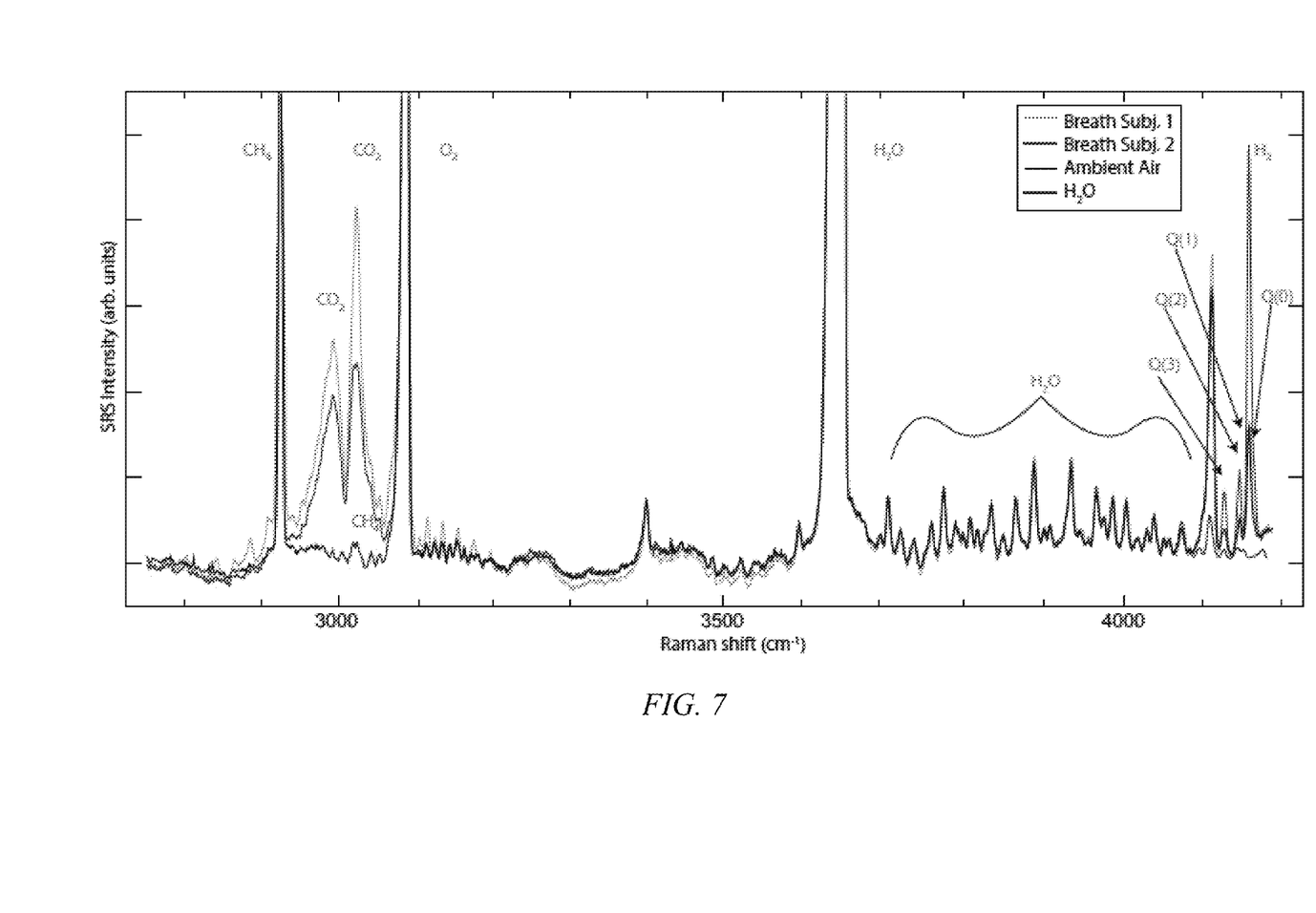
FIG. 7 illustrates a comparison between two breath samples and ambient laboratory air, wherein hydrogen is detected in ambient air and in breath near 4160 cm$^{-1}$, in accordance with an embodiment of the present invention.

To examine in more detail the features from trace constituents, FIG. 7 shows a magnified view of the data of FIG. 6, with additional spectra for comparison. Displayed are one trace for ambient air, two traces for breath samples from different subjects, and a scaled trace recorded at 1.5% water concentration for a background reference. Most peaks seen actually originate from water SRS in spite of the use of a desiccant. The secondary bands from methane are also visible over a broad range of frequencies, most notably near 3025 cm$^{-1}$, overlapping with the oxygen O-branch overtone in the case of ambient air, as well as with the $CO_2$ band centered at 3010 cm$^{-1}$ in the case of breath.

On the right end of FIG. 7, the SRS spectral signature of hydrogen is evident for both ambient air and for breath. The Q(0) line (4163 cm$^{-1}$) and the Q(1) line (4157 cm$^{-1}$) mostly overlap at the detection resolution but the Q(2) line (4145 cm$^{-1}$) and the Q(3) line (4128 cm$^{-1}$) are seen separately. When the chamber is not dried out with desiccant, it is revealed that the hydrogen lines very nearly overlap with secondary water lines constituting a background signal. Therefore, the residual concentration of water is the dominant limiting factor when it comes to the ability to detect hydrogen at trace concentrations, at least at the spectral resolution of the setup. In principle, hydrogen detection could still be performed without a desiccant as long as an adequate background subtraction can be performed. It is noted that the peaks near 3400 cm$^{-1}$ and near 4100 cm$^{-1}$ likely originate in grating 'ghost' diffraction related to oxygen and nitrogen, respectively (they are not from light at this actual frequency and can be removed with a long pass filter).

Figure 8:
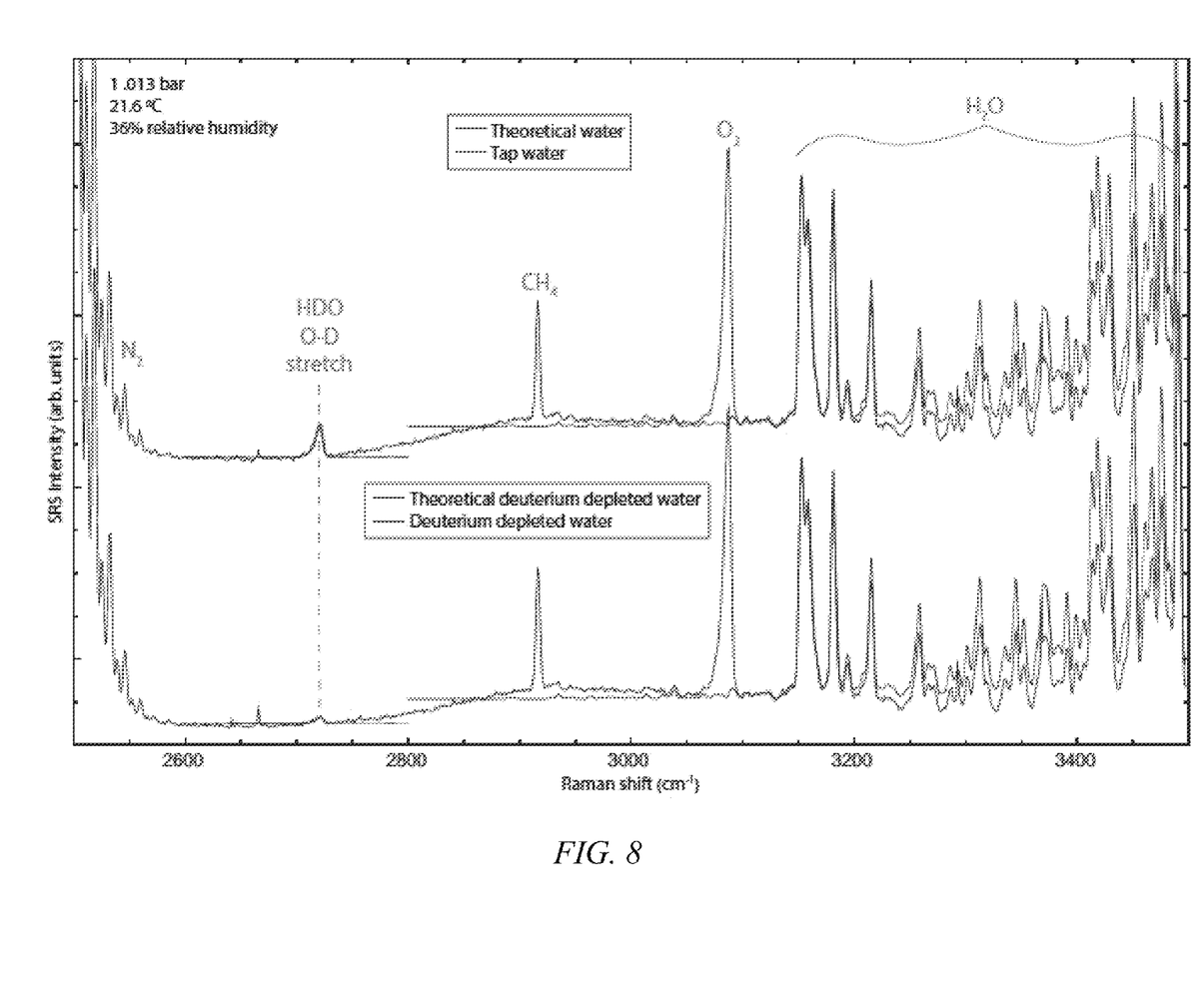
FIG. 8 illustrates the Raman spectra of air at atmospheric pressure in the presence of a liquid water sample beneath the multipass cavity foci (10 min exposure), wherein the HDO (semiheavy water $^1H^2H^{16}O$) peak near 2721 cm$^{-1}$ is about five times greater in the tap water sample than in a sample of 'deuterium-depleted' water, in accordance with an embodiment of the present invention.

Lastly, FIG. 8 illustrates high isotopic selectivity at trace concentrations, using as an example water vapor, which can be easily obtained in various isotopologue mixtures. Furthermore, to demonstrate instrument portability, measurements were performed with an inexpensive CMOS camera maintained at −25° C., in conjunction with a holographic diffraction grating. The spectral resolution afforded by this setup is approximately 5 cm$^{-1}$. The focus was on semi-heavy water, HDO, naturally found with a relative abundance of 0.0315%. Operating the chamber at atmospheric pressure, a liquid water sample was introduced below the multipass cavity foci. In that way the headspace evaporation is detected. Unwanted residual background water vapor is absorbed by the desiccant.

Two different samples were investigated: local tap water and 'deuterium-depleted' commercial potable water ("Litewater") with a certified D/H ratio of 5 ppm. The peak near 2721 cm$^{-1}$ associated with O—D bond stretching provides a distinct spectral signature for the identification of HDO. To explicitly indicate the spectral features associated with water in FIG. 8 a trace was generated based on previously tabulated information. Specifically, the therein reported water Raman differential scattering cross-sections were utilized to define the magnitude of lorentzian lineshapes convolved with an instrument response function such that the overall spectral resolution was 5 cm$^{-1}$. In FIG. 8 it is evident that the HDO peak is reduced for the 'deuterium-depleted' water compared to tap water, as expected. This reduction corresponds to a HDO concentration diminished from 5.4 to 0.9 ppm in atmospheric air. HDO plays an important role in mapping the natural water cycle, which is currently done with expensive detection systems such as those based on cavity-ring down spectroscopy. Clearly, the multipass cavity offers an exceptionally low detection limit that is on the order of 100 ppb even without pressurization and compares favorably with existing approaches. Crucially, this low detection limit is afforded for isotopologues, which could be of interest for example for the urea breath test, and possibly for other components of the human volatilome.

The data of FIG. 7 and FIG. 8 allows one to extract meaningful thresholds of detection of a given substance in a realistic environment, such as is relevant for respiratory breath. Breath analysis is a valuable tool in established medical tests such as the hydrogen breath test or tests involving metabolic tracing of isotopically labeled ingested food. It may also find use in early and inexpensive detection of lung infections. The experiments demonstrate the suitability of SRS for all these applications because of the high sensitivity and versatility afforded.

Table 2 below summarizes information regarding the chemical species detected with our method, as well as species that are potentially detectable at the concentration listed. The table includes the typical concentration for a given molecule as reported in prior literature, as well as the concentration extracted from a data based on peak intensities and tabulated differential scattering cross sections. Experimental peak intensities were based on the areas under a given peak and ratios with the area under the nitrogen Raman peak were computed. A limit of detection (LOD) for selected molecules is also listed in Table 2.

TABLE 2

Comparison of nominal and measured concentrations of various gases and their limit of detection (LOD) for a 300 s exposure time.

| Gas | Raman shift ($cm^{-1}$) | Cross section at $\lambda_{pump}$ = 443 nm [b] | Sample | Nominal conc. (ppm) | Measured conc. (ppm) [c] | LOD (ppm) |
|---|---|---|---|---|---|---|
| $O_2$ | 1556 | 1.16 | air | $2.095(10)^5$ | — | — |
|  |  |  | breath | $\sim 1.6(10)^5$ | $1.7(10)^5$ | — |
| $CO_2$ | 1388 | 1.20 | air | 415 | 451 | 24 [a] |
|  |  |  | breath | $\sim 3.8(10)^4$ | $4.8(10)^4$ | 24 [a] |
| $CH_4$ | 2917 | 7.64 | air | 1.9 | 2.1 | 0.10 |
|  |  |  | breath | $\sim 2$ | 2.1 | 0.10 |
| $H_2$ | 4160 | 2.80 | air | 0.6 | 0.4 | 0.04 |
|  |  |  | breath | $\sim 1$ | 3.1 | 0.04 |
| $NH_3$ | 3334 | 4.36 | breath | $\sim 1$ | — | 0.11 |
| CO | 2145 | 0.93 | breath | $\sim 1$ | — | 37 |
| NO | 1876 | 0.33 | breath | — | — | 5.1 |
| $NO_2$ | 1320 | 15.8 | breath | — | — | 0.13 |
| $N_2O$ | 1285 | 2.20 | air | .33 | — | 13.2 |
| $C_2H_2$ | 1342 | 6.65 | air | — | — | 0.38 |
| $(CH_3)_2CO$ | 2934 | 10.3 | breath | $\sim 1$ | — | 0.56 |

[a] 5 s exposure.
[b] Relative to the $v_1$ band in $N_2$ [35].
[c] Referenced to the nominal oxygen concentration.

The high-quality spectra of FIG. 7 and FIG. 8 also permit placement of an upper bound on the concentration of undetected species. For example, ammonia ($NH_3$) has a Raman band near 3334 $cm^{-1}$ with a scattering cross section close to that of methane. Using three times the average noise intensity at that frequency as a detection threshold one can estimate that if ammonia was present in the chamber loaded with a breath sample, it must have been at concentrations below 100 ppb. Since typical ammonia concentrations in breath are on the order of 400 ppb, it is possible that ammonia losses are incurred during the sample loading process, perhaps due to chemical reactions. Further investigations will be required for clarification.

Similarly, one can place detection limits on other substances such as carbon monoxide, nitrogen oxides or volatile organic compounds (VOCs) like acetone, as listed in Table 2. The concentration of acetone appears to vary significantly in breath compared to methane or hydrogen and was not detected in the samples under consideration here. Ethene ($C_2H_2$) which plays an important role in industrial fruit ripening, should be detectable in air at <1 ppm concentration. Nitric oxide (NO) and nitrogen dioxide ($NO_2$), free radicals indicative of pulmonary inflammation may be detected at an even lower concentration. Finally, nitrous oxide ($N_2O$), a potent greenhouse gas with a steadily increasing concentration in air, is potentially detectable at ~10 ppm levels.

It may seem that the detection at even lower concentrations will become limited by the dominating presence of secondary peaks from substances present at higher concentrations such as $O_2$, $N_2$ and even $CO_2$. For instance, the spectral signature of carbon monoxide in breath falls amid the nitrogen O-branch. However, the width of individual peaks is limited here by the spectral detection apparatus (7 $cm^{-1}$). Were it limited by the laser linewidth (3.5 $cm^{-1}$) or by the intrinsic transition linewidth (~0.1 $cm^{-1}$), substantial gains in resolving power would be anticipated with improved detection resolution and/or laser spectral purity. It should also be noted that pressure may be increased by at least an order of magnitude, although deviations from ideal gas behavior will then need to be taken into account for accurate retrieval of analyte concentrations. Pressure induced spectral broadening on the other hand is not expected to be a limitation at the current detection resolution.

As such, the simultaneous measurement, via SRS, of concentrations of $N_2$, $O_2$, $CO_2$, $H_2O$, $CH_4$, $H_2$, and isotopologues thereof, in both ambient air and in human breath, with trace sensitivity, is provided. Based on a peak intensity analysis of rovibrational bands associated with these chemical species a LOD as low as 30 ppb for $H_2$ was obtained for a 5 min long exposure time. This was enabled by a combination of sample pressurization up to 10 bar and a feedback generating multipass cavity. The measurements presented show the suitability of SRS for comparatively low-cost gas concentration measurements in a realistic setting in which a device would operate, as opposed to manufactured, dry, pre-mixed bottled gases. With improvements, such as with the employment of ultra-low loss mirrors and a modest increase in laser power, detection limits below 10 ppb ought to be achievable. This would enable for example the detection of a number of additional VOCs the concentration of which in breath is typical on the order of 50 ppb.

Figure 9:
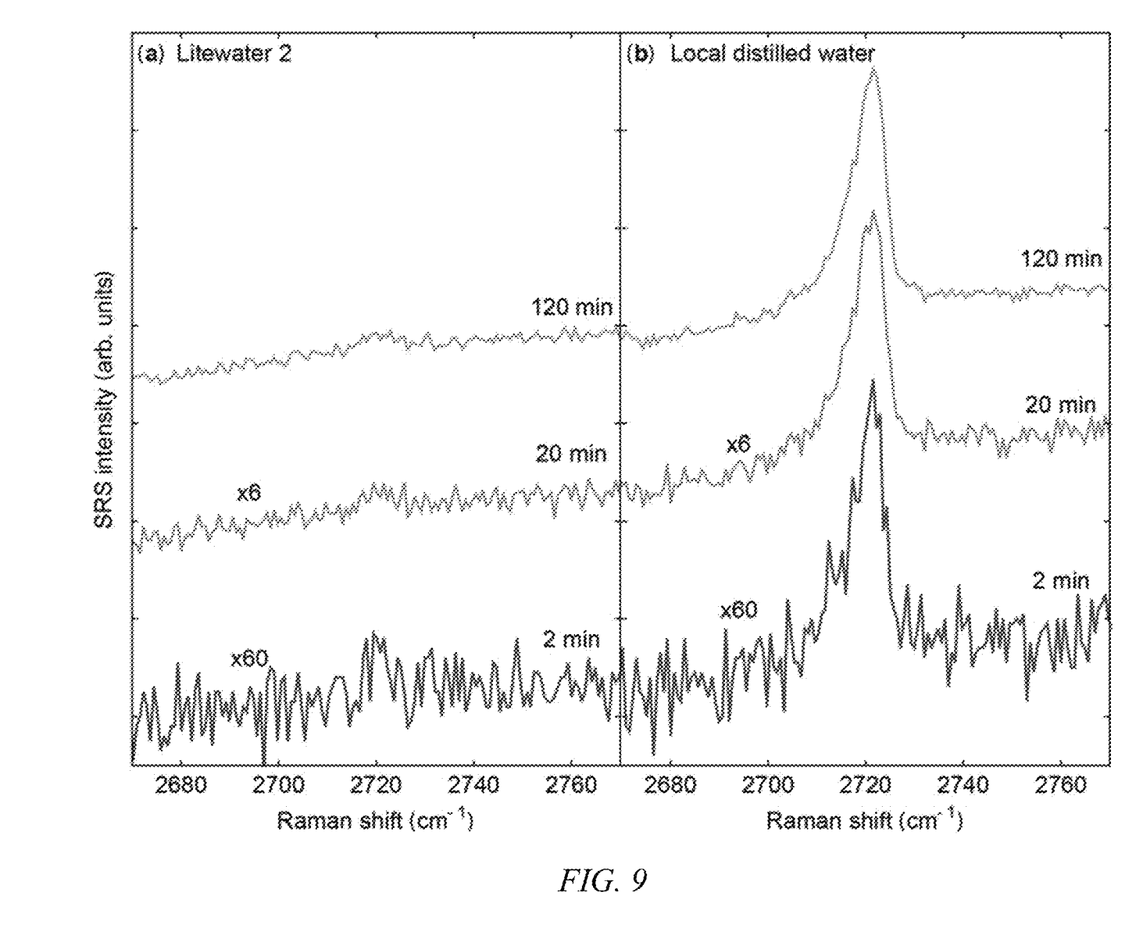
FIG. 9 illustrates (a) SRS spectra for 'deuterium-depleted' water at exposure (integration) times of 2×60 s (bottom), 20×60 s (middle) and 120×60 s (top). (b) SRS spectra for local distilled water at exposure (integration) times of 2×60 s (bottom) 20×60 s (middle) and 120×60 s (top). Traces have been offset for clarity.

In an additional embodiment, cavity-enhanced spontaneous Raman scattering was investigated as a means of simple and inexpensive isotopic water analysis. The actual limit of detection depends on exposure (integration time), as illustrated in FIG. 9. Random noise in signal and background are substantially reduced when the total exposure time is increased from order one minute to order one hour. Exposure times of several hours are beneficial, but not critical to further decrease noise. In this embodiment, isotopic water analysis was investigated which enables trace detection down to a deuterium concentration of a few parts-per-million. This was achieved with the feedback multipass Raman scattering under atmospheric pressure as described with reference to FIG. 5 (headspace evaporation from a liquid sample) with the actual HDO concentration in air well below 1 ppm and total measurement duration of order 1 hour. As an inexpensive approach with all components operating at room temperature, it could be deployed for field measurements and complement existing techniques such as cavity-ringdown spectroscopy. As a Raman scattering technique, it simultaneously allows the detection of dozens of other chemical species.

Accordingly, in various embodiments, the present invention provides a simple, robust and highly effective SRS trace gas detection system and associated method of use. The system consists of a large external cavity multimode diode laser incorporating a multipass cavity with frequency selection. Under ambient atmospheric conditions, detection limits on the order of 1 ppm or less were demonstrated.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween. Now that the invention has been described,

What is claimed is:

1. A gas sensor system comprising:
   a bidirectional multipass cavity to receive a sample gas;
   a multimode laser diode to emit a laser light beam, the beam having a laser linewidth;
   an aspheric lens positioned to collimate the beam emitted from the laser diode along a fast diverging axis;
   a cylindrical mirror positioned to receive the beam from the aspheric lens, to remove divergence along a slow diverging axis of the beam and to remove astigmatism of the beam;
   a diffraction grating to receive the beam reflected from cylindrical mirror, to reduce the linewidth of the beam and to feedback the beam having the reduced linewidth to the multimode laser diode;
   a focusing lens to receive the beam from the diffraction grating and to focus the beam into the bidirectional multipass cavity; and
   a spectral analyzer to collect spectra of spontaneous Raman scattering from the interaction of the beam with the sample gas.

2. The system of claim 1, wherein the bidirectional multipass cavity comprises a first concave spherical mirror and a second concave spherical mirror positioned in near concentric arrangement.

3. The system of claim 2, wherein the beam is reflected between the first mirror and the second mirror approximately 80 times through the gas sample and cross at two slightly longitudinally offset foci to generate a high intensity beam that is returned to the focusing lens.

4. The system of claim 2, wherein the first concave spherical mirror and the second concave spherical mirror of the multipass cavity have a radius of curvature of about 50 mm.

5. The system of claim 2, wherein the first concave spherical mirror is separated from the second concave spherical mirror by about 97 mm.

6. The system of claim 1, wherein the multimode laser diode is a semiconductor laser diode.

7. The system of claim 1, wherein the multimode laser diode is a 443 nm GaN diode rated at up to 6 W.

8. The system of claim 2, wherein the aspheric lens has a numerical aperture of about 0.5 and an effective focal length of about 4 mm.

9. The system of claim 2, wherein the cylindrical mirror has a focal length of about 40 CM.

10. The system of claim 1, wherein the spectral analyzer is positioned collinearly with the multimode diode laser and the spectral analyzer comprises a dichroic filter to collinearly extract forward and backward Raman scattered light.

11. The system of claim 1, wherein the diffraction grating is a volume Bragg grating.

12. The system of claim 1, further comprising a bandpass filter positioned to remove florescence from the laser diode or from one or more optical components traversed by light returning from the multipass cavity.

13. The system of claim 1, further comprising a tilted bandpass filter positioned to reflect the Raman scattered light returning from the multipass cavity.

14. The system of claim 1, further comprising a long pass filter positioned in a Raman collection path to remove background light and background light generated by the residual laser reflections.

15. The system of claim 1, further comprising a pressurization box, wherein the multipass cavity is positioned within the pressurization box.

16. A method for trace gas sensing, the method comprising:
   introducing a sample gas into a bidirectional multipass cavity;
   coupling a laser light beam emitted from a multimode laser diode to the multipass cavity, the beam having a laser linewidth;
   collimating the beam emitted from the laser diode along a fast diverging axis using an aspheric lens;
   removing divergence along a slow diverging axis of the beam and removing astigmatism of the beam using a cylindrical mirror positioned to receive the beam from the aspheric lens;
   reducing the linewidth of the beam and feeding back the beam having the reduced linewidth to the laser diode using a diffraction grating to receive the beam reflected from cylindrical mirror;
   focusing the beam from the diffraction grating using a focusing lens to couple the beam into the bidirectional multipass cavity; and
   collecting spectra of spontaneous Raman scattering from the interaction of the beam with the sample gas in the multipass cavity using a spectral analyzer.

17. The method of claim 16, wherein the bidirectional multipass cavity comprises a first concave spherical mirror and a second concave spherical mirror positioned in near concentric arrangement.

18. The method of claim 17, wherein the beam is reflected between the first mirror and the second mirror approximately 80 times through the gas sample and cross at two slightly longitudinally offset foci to generate a high intensity beam that is returned to the focusing lens.

19. The method of claim 17, wherein the first concave spherical mirror and the second concave spherical mirror of the multipass cavity have a radius of curvature of about 50 mm and wherein the first concave spherical mirror is separated from the second concave spherical mirror by about 97 mm.

20. The method of claim 1, wherein the multipass cavity is positioned within a pressurization box.

* * * * *